US009677079B2

(12) United States Patent
Matlack et al.

(10) Patent No.: US 9,677,079 B2
(45) Date of Patent: Jun. 13, 2017

(54) YEAST CELLS EXPRESSING AMYLOID BETA AND USES THEREFOR

(75) Inventors: Kent E. S. Matlack, San Francisco, CA (US); Susan L. Lindquist, Cambridge, MA (US); Sebastian Treusch, San Francisco, CA (US)

(73) Assignee: Whitehead Insititute for Biomedical Research, Cambridge, MA (US)

( * ) Notice: Subject to any disclaimer, the term of this patent is extended or adjusted under 35 U.S.C. 154(b) by 947 days.

(21) Appl. No.: 13/521,966

(22) PCT Filed: Jan. 11, 2011

(86) PCT No.: PCT/US2011/020879
§ 371 (c)(1),
(2), (4) Date: Oct. 4, 2012

(87) PCT Pub. No.: WO2011/088059
PCT Pub. Date: Jul. 21, 2011

(65) Prior Publication Data
US 2013/0022988 A1    Jan. 24, 2013

Related U.S. Application Data

(60) Provisional application No. 61/294,282, filed on Jan. 12, 2010.

(51) Int. Cl.
*C12N 15/81* (2006.01)
*C07K 14/47* (2006.01)

(52) U.S. Cl.
CPC .......... *C12N 15/81* (2013.01); *C07K 14/4711* (2013.01)

(58) Field of Classification Search
None
See application file for complete search history.

(56) References Cited

U.S. PATENT DOCUMENTS

| 2002/0068325 | A1* | 6/2002 | Ng et al. ............ 435/69.1 |
| 2005/0227322 | A1 | 10/2005 | Lindquist et al. |
| 2006/0141449 | A1 | 6/2006 | Lindquist et al. |

FOREIGN PATENT DOCUMENTS

| CN | 101492674 | 7/2009 |
| WO | WO2008/084254 | 7/2008 |

OTHER PUBLICATIONS

Klein et al., Proc. Natl. Acad. Sci., 93:7108-7113, 1996.*
Cereghino et al., FEMS Micro. Rev., 24:45-66, 2000.*
Culvenor et al., "Subcellular localization of the Alzheimer's disease amyloid precursor protein and derived polypeptides expressed in a recombinant yeast system." Amyloid, 1998, vol. 5, No. 2. pp. 79-89. Abstract only.
Hines et al., "The expression and processing of human beta-amyloid peptide precursors in *Saccharomyces cerevisiae*: evidence for a novel endopeptidase in the yeast secretory system." Cell Mol. Biol. Res., 1994. vol. 40, No. 4, pp. 273-284. Abstract only.
Jung et al., "Increased viability of PC12 cells exposed to amyloid-b peptide by transduction with human TAT-methionine sulfoxide reductase." Neuroreport, Dec. 2003, vol. 14, No. 18, p. 2349-2353.
PCT International Search Report and Written Opinion in corresponding PCT Application No. PCT/US2011/20879 dated Apr. 12, 2011.
pPICZalpha Vector, vector map, http://plasmid.med.harvard.edu/PlasmidRepository/file/map/ppiczalpha_abc.pdf, retrieved from internet on Jun. 27, 2014.
Chacinska, A. et al., "Effects of beta-amyloid on proliferation and morphology of yeast *Saccharomyces cerevisiae*," *Letters in Peptide Science* (2002), 9(4-5):197-201.
Shen, M. et al., "Expression, purification and characterization of recombinant human beta-amyloid 1-42 in Pichia pastoris," *Protein Expression and Purification, Academic Press* (2009), 63(2):84-88.
Treusch, S. et al., "Functional Links Between Aβ Toxicity, Endocytic Trafficking, and Alzheimer's Disease Risk Factors in Yeast," *Science* (2011),334(6060):1241-1245.
Ma, J. et al., "De novo generation of $PrP^{Sc}$-like conformation in living cells", *Nature Cell Biology* (1999) vol. 1, pp. 358-361.

* cited by examiner

*Primary Examiner* — Nancy Treptow
(74) *Attorney, Agent, or Firm* — Fish & Richardson P.C.

(57) ABSTRACT

Disclosed are yeast cells expressing a polypeptide comprising a signal sequence and a human amyloid beta protein. Also disclosed are methods of screening yeast cells to identify compounds that prevent or suppress amyloid beta-induced toxicity and genetic suppressors or enhancers of amyloid beta-induced toxicity. Compounds identified by such screens can be used to treat or prevent neurodegenerative disorders such as Alzheimer's disease.

21 Claims, 5 Drawing Sheets

SEQUENCE LISTING

<160> NUMBER OF SEQ ID NOS: 13

<210> SEQ ID NO 1
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

-continued

```
Met Phe Phe Asn Arg Leu Ser Ala Gly Lys Leu Leu Val Pro Leu Ser
1               5                   10                  15

Val Val Leu Tyr Ala Leu Phe Val Val Ile Leu Pro Leu Gln Asn Ser
                20                  25                  30

Phe His Ser Ser Asn Val Leu Val Arg Gly Asp Ala Glu Phe Arg His
            35                  40                  45

Asp Ser Gly Tyr Glu Val His His Gln Lys Leu Val Phe Phe Ala Glu
        50                  55                  60

Asp Val Gly Ser Asn Lys Gly Ala Ile Ile Gly Leu Met Val Gly Gly
65                  70                  75                  80

Val Val Ile Ala

<210> SEQ ID NO 2
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
acaagtttgt acaaaaaagc aggcttcaca aaatgttttt caacagacta agcgctggca      60
agctgctggt accactctcc gtggtcctgt acgccctttt cgtggtaata ttacctttac     120
agaattcttt ccactcctcc aatgttttag ttagaggtga tgctgaattt agacatgatt     180
ctggttatga agttcatcat caaaaattgg ttttttttgc tgaagatgtt ggttctaata     240
aaggtgctat tattggtttg atggttggtg gtgttgtcat tgcttaaacc cagcttctt     300 gtacaaagtg gt                                                        312

<210> SEQ ID NO 3
<211> LENGTH: 43
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala Thr
            35                  40

<210> SEQ ID NO 4
<211> LENGTH: 43
<212> TYPE: PRT
<213> ORGANISM: Homo sapiens

<400> SEQUENCE: 4

Asp Thr Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala Thr
            35                  40

<210> SEQ ID NO 5
<211> LENGTH: 43
<212> TYPE: PRT
```

<213> ORGANISM: Homo sapiens

<400> SEQUENCE: 5

Asp Ala Glu Phe Arg Arg Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 6
<211> LENGTH: 43
<212> TYPE: PRT
<213> ORGANISM: Homo sapiens

<400> SEQUENCE: 6

Asp Ala Glu Phe Arg His Asn Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 7
<211> LENGTH: 43
<212> TYPE: PRT
<213> ORGANISM: Homo sapiens

<400> SEQUENCE: 7

Asp Ala Glu Phe Arg His Asp Ser Gly Tyr Glu Val His His Gln Lys
1               5                   10                  15

Leu Val Phe Phe Gly Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 8
<211> LENGTH: 43
<212> TYPE: PRT
<213> ORGANISM: Homo sapiens

<400> SEQUENCE: 8

Asp Ala Glu Phe Arg His Asp Ser Gly Tyr Glu Val His His Gln Lys
1               5                   10                  15

Leu Val Phe Phe Ala Gly Asp Val Gly Ser Asn Lys Gly Ala Ile Ile
            20                  25                  30

Gly Leu Met Val Gly Gly Val Val Ile Ala Thr
        35                  40

<210> SEQ ID NO 9
<211> LENGTH: 43
<212> TYPE: PRT
<213> ORGANISM: Homo sapiens

<400> SEQUENCE: 9

Asp Ala Glu Phe Arg His Asp Ser Gly Tyr Glu Val His His Gln Lys
1               5                   10                  15

Leu Val Phe Phe Ala Gln Asp Val Gly Ser Asn Lys Gly Ala Ile Ile
            20                  25                  30

```
Gly Leu Met Val Gly Gly Val Val Ile Ala Thr
        35                  40
```

<210> SEQ ID NO 10
<211> LENGTH: 43
<212> TYPE: PRT
<213> ORGANISM: Homo sapiens

<400> SEQUENCE: 10

```
Asp Ala Glu Phe Arg His Asp Ser Gly Tyr Glu Val His His Gln Lys
1               5                   10                  15

Leu Val Phe Phe Ala Lys Asp Val Gly Ser Asn Lys Gly Ala Ile Ile
            20                  25                  30

Gly Leu Met Val Gly Gly Val Val Ile Ala Thr
        35                  40
```

<210> SEQ ID NO 11
<211> LENGTH: 43
<212> TYPE: PRT
<213> ORGANISM: Homo sapiens

<400> SEQUENCE: 11

```
Asp Ala Glu Phe Arg His Asp Ser Gly Tyr Glu Val His His Gln Lys
1               5                   10                  15

Leu Val Phe Phe Ala Glu Asn Val Gly Ser Asn Lys Gly Ala Ile Ile
            20                  25                  30

Gly Leu Met Val Gly Gly Val Val Ile Ala Thr
        35                  40
```

<210> SEQ ID NO 12
<211> LENGTH: 43
<212> TYPE: PRT
<213> ORGANISM: Homo sapiens

<400> SEQUENCE: 12

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Thr Thr
        35                  40
```

<210> SEQ ID NO 13
<211> LENGTH: 43
<212> TYPE: PRT
<213> ORGANISM: Homo sapiens

<400> SEQUENCE: 13

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Val Thr
        35                  40
```

YEAST CELLS EXPRESSING AMYLOID BETA AND USES THEREFOR

CROSS REFERENCE TO RELATED APPLICATIONS

This application is a national phase filing under 35 U.S.C. §371 of International application number PCT/US2011/020879, filed Jan. 11, 2011, which claims priority from provisional application No. 61/294,282 filed Jan. 12, 2010. The entire content of the prior applications are incorporated herein by reference in their entirety.

TECHNICAL FIELD

The invention relates to protein chemistry and cellular and molecular biology

BACKGROUND

Alzheimer's disease is a neurodegenerative disorder characterized by neurofibrillary tangles and plaques containing an amyloid beta peptide. Patients with Alzheimer's disease exhibit progressive dementia and personality dysfunction. Proteolytic cleavage of the amyloid precursor protein (APP) results in the generation of an amyloid beta peptide having a length ranging from 38 to 43 amino acids. The amyloid beta 1-42 peptide is particularly prone to self-aggregation and is strongly linked to development of Alzheimer's disease.

SUMMARY

The invention is based, at least in part, on the discovery that a fusion polypeptide containing a signal sequence and a human amyloid beta protein is toxic when expressed in a yeast cell. This discovery permits the carrying out of screening assays using amyloid beta-expressing yeast cells to identify compounds or genetic factors that modulate amyloid beta-induced toxicity. Compounds identified by such screens can be used for the treatment or prevention of neurodegenerative diseases such as Alzheimer's disease.

Described herein is a yeast cell comprising an expression construct comprising a promoter operably linked to a nucleic acid encoding a polypeptide comprising a signal sequence and a human amyloid beta protein, wherein expression of the nucleic acid and production of the polypeptide in the cell results in a decrease in growth or viability of the cell. In some embodiments, expression of the nucleic acid and production of the polypeptide renders the yeast cell non-viable.

A signal sequence causes a polypeptide to be targeted to the endoplasmic reticulum within a cell. In some embodiments, the signal sequence is located at the amino terminus of the polypeptide encoded by the expression construct. In some embodiments, the signal sequence is one that directs co-translational transport of the encoded polypeptide.

The signal sequence can be identical to a naturally occurring signal sequence or can be an artificial (non-naturally occurring) signal sequence. In some embodiments, the signal sequence is identical to the signal sequence of a naturally occurring yeast protein (e.g., identical to the yeast Kar2p signal sequence). In some embodiments, the signal sequence is identical to the signal sequence of a naturally occurring mammalian protein (e.g., a human protein).

The term "human amyloid beta protein" includes naturally occurring wild type amyloid beta peptides as well as naturally occurring mutant amyloid beta peptides. Wild type amyloid beta peptides include amyloid beta 1-38, amyloid beta 1-39, amyloid beta 1-40, amyloid beta 1-41, amyloid beta 1-42, and amyloid beta 1-43. Amyloid beta mutations include A2T, H6R, D7N, A21G, E22G (Arctic), E22Q (Dutch), E22K (Italian), D23N (Iowa), A42T, and A42V (wherein the numbering is relative to the amyloid beta peptide of SEQ ID NO:3). These mutations may optionally be present in any of the amyloid beta peptides 1-38, 1-39, 1-40, 1-41, 1-42, and 1-43.

In alternate embodiments, a variant of a human amyloid beta protein can be used. A "variant human amyloid beta protein" differs (via substitution, deletion, and/or insertion) from a naturally occurring amyloid beta peptide at up to 10 amino acids (e.g., differs at no more than 5 amino acids, differs at no more than 4 amino acids, differs at no more than 3 amino acids, differs at no more than 2 amino acids, or differs at 1 amino acid) and retains the ability to cause a decrease in growth or viability of a yeast cell when expressed in a fusion polypeptide described herein.

In some embodiments, the signal sequence is identical to the signal sequence of a naturally occurring yeast protein (e.g., the signal sequence is identical to the yeast Kar2p signal sequence) and the human amyloid beta protein is wild type amyloid beta 1-42. For example, the polypeptide can comprise or consist of the amino acid sequence of SEQ ID NO:1. Exemplary nucleic acids encoding the amino acid sequence of SEQ ID NO:1 include SEQ ID NO:2 and nucleotides 33 to 284 of SEQ ID NO:2.

In some embodiments, the polypeptide encoded by an expression construct described herein is no more than 150, 125, or 100 amino acids in length.

In some embodiments, the human amyloid beta protein portion of the polypeptide encoded by an expression construct described herein is no more than 75, 50, or 45 amino acids in length.

In some embodiments, the polypeptide encoded by an expression construct described herein consists of a signal sequence and a human amyloid beta protein. In some embodiments, the polypeptide encoded by an expression construct described herein consists of a signal sequence, a linker peptide sequence, and a human amyloid beta protein.

In some embodiments, cleavage of the human amyloid beta protein portion of the polypeptide may occur before translation of the entire polypeptide is complete. This phenomenon is encompassed by the phrase "production of the polypeptide in the cell results in a decrease in growth or viability of the cell," so long as at least the human amyloid beta protein portion of the polypeptide is translated and results in a decrease in growth or viability of the cell.

In addition to a signal sequence and a human amyloid beta protein, the polypeptide encoded by an expression construct described herein can also contain one or more heterologous peptide sequences, such as an expression tag. A heterologous peptide sequence can be present at the amino terminus of the polypeptide, between the signal sequence and the human amyloid beta protein, and/or at the carboxy terminus of the polypeptide.

An expression construct described herein can optionally be integrated in the genome of the yeast cell. For example, the expression construct can be an integrative plasmid such as pRS303, pRS304, pRS305, pRS306, or a derivative thereof.

A yeast cell can have one or more (e.g., at least two, at least three, or at least four) copies (e.g., integrated copies) of an expression construct.

The promoter can be an inducible promoter such as GAL1-10, GAL1, GALL, GALS, GPD, ADH, TEF, CYC1, MRP7, MET25, TET, VP16, or VP16-ER. Alternatively, the promoter can be a constitutively active promoter.

The polypeptide can be a fusion protein containing a detectable protein (e.g., a fluorescent protein, an enzyme, or an epitope). Exemplary fluorescent proteins include red fluorescent protein, green fluorescent protein, blue fluorescent protein, yellow fluorescent protein, and cyan fluorescent protein.

In some embodiments, the yeast is *Saccharomyces cerevisiae, Saccharomyces uvae, Saccharomyces kluyveri, Schizosaccharomyces pombe, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., or *Geotrichum fermentans*.

In some embodiments, at least one gene that encodes a protein involved in drug efflux or cell permeability is disrupted in the yeast cell. For example, one or more of the genes PDR1, PDR3, PDR5, SNQ2, or ERG6 can be disrupted in the yeast cell.

Also disclosed is a method of inducing toxicity in a yeast cell by: providing a yeast cell described herein; and inducing a level of expression of the nucleic acid in the yeast cell that is toxic to the yeast cell.

Also disclosed is a method of identifying a compound that prevents or suppresses amyloid beta-induced toxicity by: culturing a yeast cell described herein in the presence of a candidate agent and under conditions that allow for expression of the nucleic acid at a level that, in the absence of the candidate agent, is sufficient to induce toxicity in the cell; measuring cell growth or viability in the presence of the candidate agent; and comparing cell growth or viability measured in the presence of the candidate agent to cell growth or viability in the absence of the candidate agent, wherein if cell growth or viability is increased in the presence of the candidate agent as compared to in the absence of the candidate agent, then the candidate agent is identified as a compound that prevents or suppresses amyloid beta-induced toxicity.

Also disclosed is a method of identifying a genetic suppressor or enhancer of amyloid beta-induced toxicity by: providing a yeast cell described herein, wherein the yeast cell has been genetically modified to overexpress a gene; culturing the yeast cell under conditions that allow for expression of the protein at a level that, in the absence of overexpression of the gene, is sufficient to induce toxicity in the yeast cell; measuring cell growth or viability in the presence of overexpression of the gene; and comparing cell growth or viability measured in the presence of overexpression of the gene to cell growth or viability in the absence of overexpression of the gene, wherein (i) if cell growth or viability is increased in the presence of overexpression of the gene as compared to in the absence of overexpression of the gene, then the gene is identified as a genetic suppressor of amyloid beta-induced toxicity, and (ii) if cell growth or viability is decreased in the presence of overexpression of the gene as compared to in the absence of overexpression of the gene, then the gene is identified as a genetic enhancer of amyloid beta-induced toxicity.

Also disclosed is a method of identifying a genetic suppressor or enhancer of amyloid beta-induced toxicity by: providing a yeast cell described herein, wherein an endogenous gene of the yeast cell has been disrupted; culturing the yeast cell under conditions that allow for expression of the protein at a level that, in the absence of disruption of the endogenous gene, is sufficient to induce toxicity in the yeast cell; measuring cell growth or viability in the presence of disruption of the endogenous gene; and comparing cell growth or viability measured in the presence of disruption of the endogenous gene to cell growth or viability in the absence of disruption of the endogenous gene, wherein (i) if cell growth or viability is increased in the presence of disruption of the endogenous gene as compared to in the absence disruption of the endogenous gene, then the gene is identified as a genetic enhancer of amyloid beta-induced toxicity, and (ii) if cell growth or viability is decreased in the presence of disruption of the endogenous gene as compared to in the absence disruption of the endogenous gene, then the gene is identified as a genetic suppressor of amyloid beta-induced toxicity. As an alternative to use of a yeast cell that has had an endogenous gene disrupted, the method may be performed using a yeast cell wherein expression of the endogenous gene is suppressed by use of RNA interference.

In some embodiments, of any of the methods of identifying yeast genes or identifying compounds in yeast cells, the yeast cells are cultured under at least two different culture conditions. In some embodiments, the culture conditions result in different levels of mitochondrial respiration. In some embodiments, the culture conditions comprise use of culture medium comprising glucose, galactose, or glycerol as a carbon source. In some embodiments, yeast cells are cultured under at least three different culture conditions, and a gene is identified as a genetic enhancer or suppressor of amyloid-beta induced toxicity or a compound is identified as a modulator of amyloid beta mediated toxicity (e.g., an inhibitor of amyloid beta toxicity) under at least two of the culture conditions, e.g., under three different culture conditions or all of the culture conditions tested.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
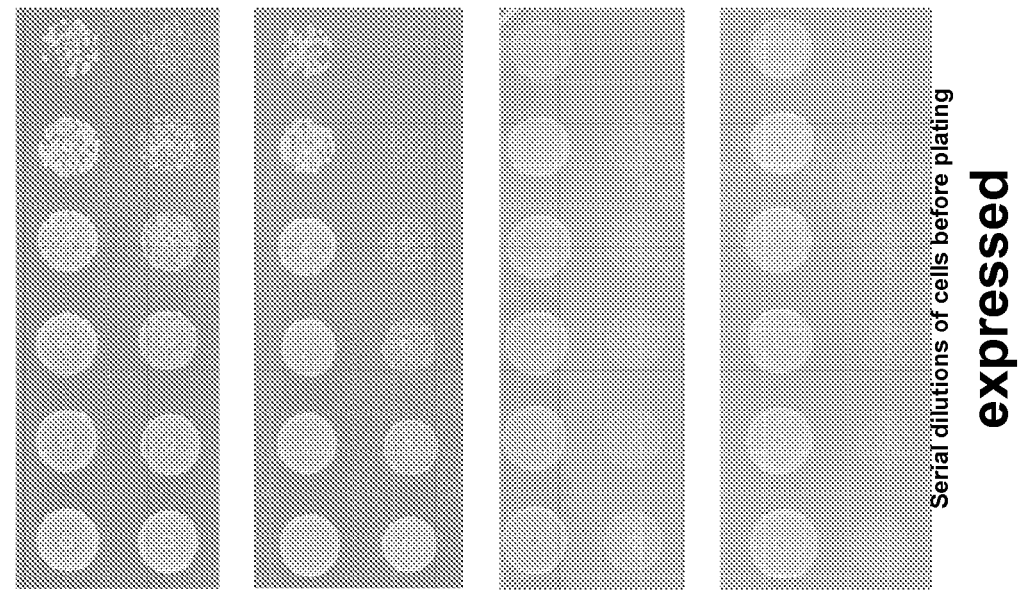
FIG. 1 is a series of photographs of yeast cells transformed with either an empty vector (top row of each photograph) or a galactose-inducible expression plasmid encoding a yeast Kar2p signal sequence/human amyloid beta 1-42 fusion polypeptide (bottom row of each photograph). The yeast cells were spotted on glucose or galactose and growth was assessed. The experimental and control transformants grew equally well on the glucose plates ("unexpressed"), whereas amyloid beta expression profoundly inhibited cell growth ("expressed") in a copy number-dependent manner.

The amyloid beta-expressing yeast cells described herein can be used to identify compounds or genetic factors that modulate amyloid beta-induced toxicity. Compounds identified by such screens can be used for the treatment or prevention of neurodegenerative diseases such as Alzheimer's disease.

Proteins and Nucleic Acids

Described herein are compositions and methods for identifying candidate compounds that prevent or suppress amyloid beta-induced toxicity and genetic suppressors or enhancers of amyloid beta-induced toxicity. A fusion polypeptide used in the compositions and methods described herein contains a signal sequence and a human amyloid beta protein.

As used herein, the term "human amyloid beta protein" refers to a sequence identical to a naturally occurring 38-43 amino acid amyloid beta peptide that is derived via proteolytic processing of the human amyloid precursor protein (APP) and is associated with amyloid pathologies. The term includes naturally occurring wild type amyloid beta peptides as well as naturally occurring mutant amyloid beta peptides. Wild type amyloid beta peptides include amyloid beta 1-38, amyloid beta 1-39, amyloid beta 1-40, amyloid beta 1-41, amyloid beta 1-42, and amyloid beta 1-43. Amyloid beta mutations include A2T, H6R, D7N, A21G, E22G (Arctic), E22Q (Dutch), E22K (Italian), D23N (Iowa), A42T, and A42V (wherein the numbering is relative to the amyloid beta peptide of SEQ ID NO:3). These mutations may optionally be present in any of the amyloid beta peptides 1-38, 1-39, 1-40, 1-41, 1-42, and 1-43.

Amino acids 1-43 of human amyloid beta, which amino acids are used as the backbone of the amyloid beta peptides described herein, are as follows: DAEFRHDSGYEVH-HQKLVFFAEDVGSNKGAIIGLMVGGVVIAT (SEQ ID NO:3).

As used herein, the term "signal sequence" refers to a peptide sequence that is present within a polypeptide and causes the polypeptide to be targeted to the endoplasmic reticulum within a cell. An exemplary signal sequence described in the working examples is the yeast Kar2p signal sequence. However, a wide variety of signal sequences are known and can be used to cause endoplasmic reticulum targeting of the fusion polypeptides described herein. Signal sequences are reviewed in e.g., Wilkinson et al. (1997) J Membr Biol. 155(3):189-97, Haguenauer-Tsapis (1992) Mol Microbiol. 6(5):573-9, and Pool (2005) Mol Membr Biol. 22(1-2):3-15.

A polypeptide containing a signal sequence and a human amyloid beta protein may optionally be fused with a second domain. The second domain of the fusion protein can optionally be an immunoglobulin element, a dimerizing domain, a targeting domain, a stabilizing domain, or a purification domain. Alternatively, an amyloid beta protein can be fused with a heterologous molecule such as a detection protein. Exemplary detection proteins include: a fluorescent protein such as green fluorescent protein (GFP), cyan fluorescent protein (CFP) or yellow fluorescent protein (YFP); an enzyme such as β-galactosidase or alkaline phosphatase (AP); and an epitope such as glutathione-S-transferase (GST) or hemagglutinin (HA). To illustrate, an amyloid beta protein can be fused to GFP at the N- or C-terminus or other parts of the amyloid beta protein. These fusion proteins provide methods for rapid and easy detection and identification of the amyloid beta protein in the recombinant yeast cell.

Also described herein are methods of preparing and transferring nucleic acids encoding an amyloid beta protein into a cell so that the cell expresses the amyloid beta protein. The term "amyloid beta nucleic acid" encompasses a nucleic acid containing a sequence encoding any of the amyloid beta proteins described herein. Exemplary amyloid beta nucleic acids include those encoding amyloid beta 1-42.

The term "nucleic acid" generally refers to at least one molecule or strand of DNA, RNA or a derivative or mimic thereof, containing at least one nucleobase, for example, a naturally occurring purine or pyrimidine base found in DNA or RNA. Generally, the term "nucleic acid" refers to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule.

Yeast Cells

Yeast strains that can be used in the compositions and methods described herein include, but are not limited to, *Saccharomyces cerevisiae*, *Saccharomyces uvae*, *Saccharo-*

*myces kluyveri, Schizosaccharomyces pombe, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., and *Geotrichum fermentans*. Although much of the discussion herein relates to *Saccharomyces cerevisiae* which ectopically expresses an abnormally processed protein, this is merely for illustrative purposes. Other yeast strains can be substituted for *S. cerevisiae*.

Certain aspects of the disclosure relate to screening methods for identifying candidate therapeutic agents (e.g., pharmaceutical, chemical, or genetic agents). The methods described herein can optionally be carried out in yeast strains bearing mutations in the ERG6 gene, the PDR1 gene, the PDR3 gene, the PDR5 gene, the SNQ2 gene, and/or any other gene which affects membrane efflux pumps and/or increases permeability for drugs.

A nucleic acid encoding a fusion polypeptide described herein may be transfected into a yeast cell using nucleic acid vectors that include, but are not limited to, plasmids, linear nucleic acid molecules, artificial chromosomes, and episomal vectors.

Three well known systems used for recombinant plasmid expression and replication in yeast cells include integrative plasmids, low-copy-number ARS-CEN plasmids, and high-copy-number 2μ plasmids. See Sikorski, "Extrachromosomal cloning vectors of *Saccharomyces cerevisiae*," in Plasmid, A Practical Approach, Ed. K. G. Hardy, IRL Press, 1993; and Yeast Cloning Vectors and Genes, Current Protocols in Molecular Biology, Section II, Unit 13.4, Eds., Ausubel et al., 1994.

An example of the integrative plasmids is YIp, which is maintained at one copy per haploid genome, and is inherited in Mendelian fashion. Such a plasmid, containing a gene of interest, a bacterial origin of replication and a selectable gene (typically an antibiotic-resistance marker), is produced in bacteria. The purified vector is linearized within the selectable gene and used to transform competent yeast cells.

An example of the low-copy-number ARS-CEN plasmids is YCp, which contains the autonomous replicating sequence (ARS1) and a centromeric sequence (CEN4). These plasmids are usually present at 1-2 copies per cell. Removal of the CEN sequence yields a YRp plasmid, which is typically present in 100-200 copies per cell. However, this plasmid is both mitotically and meiotically unstable.

An example of the high-copy-number 2μ plasmids is YEp, which contains a sequence approximately 1 kb in length (named the 2μ sequence). The 2μ sequence acts as a yeast replicon giving rise to higher plasmid copy number. However, these plasmids are unstable and require selection for maintenance. Copy number is increased by having on the plasmid a selection gene operatively linked to a crippled promoter.

A wide variety of plasmids can be used in the compositions and methods described herein. In one embodiment, the plasmid is an integrative plasmid (e.g., pRS303, pRS304, pRS305, pRS306, or a derivative thereof). See, e.g., Alberti et al. (2007) "A suite of Gateway cloning vectors for high-throughput genetic analysis in *Saccharomyces cerevisiae*" Yeast 24(10):913-19. In further embodiments, the plasmid is an episomal plasmid (e.g., p426GPD, p416GPD, p426TEF, p423GPD, p425GPD, p424GPD or p426GAL).

Regardless of the type of plasmid used, yeast cells are typically transformed by chemical methods (e.g., as described by Rose et al., 1990, Methods in Yeast Genetics, Cold Spring Harbor Laboratory Press, Cold Spring Harbor, N.Y.). The cells are typically treated with lithium acetate to achieve transformation efficiencies of approximately $10^4$ colony-forming units (transformed cells)/μg of DNA. Yeast perform homologous recombination such that the cut, selectable marker recombines with the mutated (usually a point mutation or a small deletion) host gene to restore function. Transformed cells are then isolated on selective media. Of course, any suitable means of introducing nucleic acids into yeast cells can be used.

The yeast vectors (plasmids) described herein typically contain a yeast origin of replication, an antibiotic resistance gene, a bacterial origin of replication (for propagation in bacterial cells), multiple cloning sites, and a yeast nutritional gene for maintenance in yeast cells. The nutritional gene (or "auxotrophic marker") is most often one of the following: 1) TRP1 (Phosphoribosylanthranilate isomerase); 2) URA3 (Orotidine-5'-phosphate decarboxylase); 3) LEU2 (3-Isopropylmalate dehydrogenase); 4) HIS3 (Imidazoleglycerol-phosphate dehydratase or IGP dehydratase); or 5) LYS2 (α-aminoadipate-semialdehyde dehydrogenase).

The yeast vectors (plasmids) described herein may also contain promoter sequences. A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively linked" and "operatively positioned" mean that a promoter is in a correct functional location and/or orientation in relation to a nucleic acid sequence to control transcriptional initiation and/or expression of that sequence.

A promoter may be one naturally associated with a nucleic acid sequence, as may be obtained by isolating the 5' non-coding sequences located upstream of the coding segment and/or exon. Such a promoter can be referred to as "endogenous." Alternatively, a promoter may be a recombinant or heterologous promoter, which refers to a promoter that is not normally associated with a nucleic acid sequence in its natural environment. Such promoters may include promoters of other genes and promoters not "naturally occurring." The promoters employed may be either constitutive or inducible.

For example, various yeast-specific promoters (elements) may be employed to regulate the expression of a RNA in yeast cells. Examples of inducible yeast promoters include GAL1-10, GAL1, GALL, GALS, TET, VP16 and VP16-ER. Examples of repressible yeast promoters include Met25. Examples of constitutive yeast promoters include glyceraldehyde 3-phosphate dehydrogenase promoter (GPD), alcohol dehydrogenase promoter (ADH), translation-elongation factor-1-alpha promoter (TEF), cytochrome c-oxidase promoter (CYC1), and MRP7. Autonomously replicating expression vectors of yeast containing promoters inducible by glucocorticoid hormones have also been described (Picard et al., 1990), including the glucocorticoid responsive element (GRE). These and other examples are described in Mumber et al., 1995; Ronicke et al., 1997; Gao, 2000, all incorporated herein by reference. Yet other yeast vectors containing constitutive or inducible promoters such as alpha factor, alcohol oxidase, and PGH may be used. For reviews, see Ausubel et al. and Grant et al., 1987.

In some embodiments, a yeast strain is used that allows for expression, e.g., inducible expression, from GAL promoters on carbon sources other than galactose. In some embodiments, the strain carries an integrated or episomal (e.g., plasmid-borne) gene encoding a fusion protein, wherein the Gal4 DNA binding domain is fused to a transcriptional activation domain and a regulatory domain. The fusion protein is characterized in that its ability to activate transcription is regulated by binding of a small molecule to the regulatory domain. For example, in some embodiments, the fusion protein does not activate transcription in the absence of the small molecule, whereas in the presence of the small molecule, the fusion protein activates transcription. Exemplary small molecules include, e.g., steroid hormones, wherein the corresponding regulatory domain comprises at least a portion of a receptor for the small molecule. For example, the small molecule may be an estrogen (e.g., estradiol), or analog thereof (e.g., tamoxifen), and the corresponding regulatory domain comprises at least a portion of the estrogen receptor (ER). Exemplary activation domains include, e.g., viral protein activation domains such as the herpes simplex virus protein VP16 activation domain. In some embodiments, the strain carries an integrated or episomal (e.g., plasmid-borne) gene encoding a Gal4-ER-VP16 fusion protein. Presence of an estrogen receptor ligand, e.g., estradiol, in the medium, allows for expression from GAL promoters on carbon sources other than galactose. One of skill in the art will appreciate that numerous ways exist to render expression of a molecule of interest, e.g., an amyloid beta peptide, conditional, e.g., on culture media containing galactose or other carbon sources.

Screening Assays

Certain aspects of the present disclosure provide methods of screening for a candidate drug (agent or compound) or a genetic factor that modulates amyloid beta-induced toxicity. Various types of candidate drugs may be screened by the methods described herein, including nucleic acids, polypeptides, small molecule compounds, and peptidomimetics. In some cases, genetic agents can be screened by contacting the yeast cell with a nucleic acid construct coding for a gene. For example, one may screen cDNA libraries expressing a variety of genes, to identify genes that modulate amyloid beta-induced toxicity.

For example, the identified drugs may modulate amyloid beta-induced toxicity. Accordingly, irrespective of the exact mechanism of action, drugs identified by the screening methods described herein are expected to provide therapeutic benefit to Alzheimer's disease.

In certain embodiments, screening methods described herein use yeast cells that are engineered to express an amyloid beta protein. For chemical screens, suitable mutations of yeast strains designed to affect membrane efflux pumps and increase permeability for drugs can be used. For example, a yeast strain bearing mutations in the ERG6 gene, the PDR1 gene, the PDR3 gene, and/or the PDR5 gene is contemplated of use. For example, a yeast strain bearing mutations in membrane efflux pumps (erg6, pdr1, pdr3, and/or pdr5) has been successfully used in many screens to identify growth regulators (Jensen-Pergakes K L, et al., 1998. Antimicrob Agents Chemother 42:1160-7).

Methods of the present disclosure relate to identifying compounds or genes tha modulate amyloid beta-induced toxicity. One of the strongest aspects of yeast is the possibility of performing high throughput screens that may identify genes, peptides and other compounds with the potential to ameliorate toxicity. A large number of compounds can be screened under a variety of growth conditions and in a variety of genetic backgrounds. The toxicity screen has the advantage of not only selecting for compounds that interact with amyloid beta, but also upstream or downstream targets that are not themselves cytotoxic and that are not yet identified.

In certain embodiments, candidate drugs can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd. (Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China). Combinatorial libraries are available and can be prepared. Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Several commercial libraries can be used in the screens.

Another embodiment relates to genetic screens. For example, genomic libraries and disruption libraries can be screened to find extragenic suppressors or enhancers of amyloid beta-induced toxicity. Because the yeast genome is small, 10,000 transformants of each type should be sufficient for good coverage.

Another embodiment contemplates screening assays using fluorescent resonance energy transfer (FRET). FRET occurs when a donor fluorophore is in close proximity (10-60 A) to an acceptor fluorophore, and when the emission wavelength of the first overlaps the excitation wavelength of the second (Kenworthy A K et al., 2001. Methods. 24:289-96). FRET should occur when cyan fluorescent protein (CFP) and yellow fluorescent protein (YFP) fusion proteins are actually part of the same complex.

For example, an amyloid beta protein can be fused to CFP and to YFP respectively, and integrated in the yeast genome under the regulation of a GAL1-10 promoter. Cells are grown in galactose to induce expression. Upon induction, cells produce the fusion proteins, which aggregate and bring the CFP and YFP close together. Because proteins in the aggregates are tightly packed, the distance between the CFP and YFP is less than the critical value of 100 A that is necessary for FRET to occur. In this case, the energy released by the emission of CFP will excite the YFP, which in turn will emit at its characteristic wavelength. FRET based screening can be used to identify candidate compounds including, drugs, genes or other factors that can disrupt the interaction of CFP and YFP by maintaining the proteins in a state that does not allow aggregation to occur.

One embodiment contemplates screening assays using fluorescence activated cell sorting (FACS) analysis. FACS provides the means of scanning individual cells for the presence of fluorescently labeled/tagged moiety. The method is unique in its ability to provide a rapid, reliable, quantitative, and multiparameter analysis on either living or fixed cells. For example, an amyloid beta protein can be suitably labeled, and provide a useful tool for the analysis and quantitation of protein aggregation as a result of other genetic or growth conditions of individual yeast cells as described above.

Screens (e.g., for compounds and/or for genetic suppressors or enhancers) can be carried out under a variety of different conditions. For example, a variety of different culture media can be used. Culture media can contain different carbon sources, e.g., different sugars such as glucose, glycerol, galactose, raffinose, etc. In some embodiments, multiple screens are performed using two, three, or more different culture conditions (e.g., culture media containing different carbon sources), and compounds or genes identified as "hits" under at least two different culture conditions are identified. In some embodiments, screens are performed under two or more different culture conditions (e.g., using culture media containing different carbon sources), wherein the different culture conditions (e.g., different carbon sources) result in different levels of mitochondrial respiration. For example, growth using culture media containing glucose, glycerol, or galactose result in different levels of mitochondrial respiration. In glucose, yeast cells ferment and respiration remains low until all glucose is converted to ethanol. In galactose respiration is moderately active. In glycerol, yeast cells are completely dependent on respiration for growth. In some embodiments, a screen is performed in parallel using media containing glucose, galactose, or glycerol as a carbon source.

Certain embodiments provide methods of further testing those potential drugs that have been identified in the yeast system, in other model systems. The model systems include, but are not limited to, worms, flies, mammalian cells, and in vivo animal models.

Compounds

Compounds to be screened or identified using any of the methods described herein can include various chemical classes, though typically small organic molecules having a molecular weight in the range of 50 to 2,500 daltons. These compounds can comprise functional groups necessary for structural interaction with proteins (e.g., hydrogen bonding), and typically include at least an amine, carbonyl, hydroxyl, or carboxyl group, and preferably at least two of the functional chemical groups. These compounds often comprise cyclical carbon or heterocyclic structures and/or aromatic or polyaromatic structures (e.g., purine core) substituted with one or more of the above functional groups.

In alternative embodiments, compounds can also include biomolecules including, but not limited to, peptides, polypeptides, peptidomimetics (e.g., peptoids), amino acids, amino acid analogs, saccharides, fatty acids, steroids, purines, pyrimidines, derivatives or structural analogues thereof, polynucleotides, nucleic acid aptamers, and polynucleotide analogs.

Compounds can be identified from a number of potential sources, including: chemical libraries, natural product libraries, and combinatorial libraries comprised of random peptides, oligonucleotides, or organic molecules. Chemical libraries consist of diverse chemical structures, some of which are analogs of known compounds or analogs or compounds that have been identified as "hits" or "leads" in other drug discovery screens, while others are derived from natural products, and still others arise from non-directed synthetic organic chemistry. Natural product libraries are collections of microorganisms, animals, plants, or marine organisms which are used to create mixtures for screening by: (1) fermentation and extraction of broths from soil, plant or marine microorganisms, or (2) extraction of plants or marine organisms. Natural product libraries include polypeptides, non-ribosomal peptides, and variants (non-naturally occurring) thereof. For a review, see Science 282:63-68 (1998). Combinatorial libraries are composed or large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701-707 (1997).

Identification of test compounds through the use of the various libraries herein permits subsequent modification of the test compound "hit" or "lead" to optimize the capacity of the "hit" or "lead" to prevent or suppress amyloid beta-induced toxicity and/or amyloid beta-induced aggregation.

The compounds identified above can be synthesized by any chemical or biological method. The compounds identified above can also be pure, or may be in a composition (e.g., a pharmaceutical composition) that contains one or more additional component(s), and can be prepared in an assay-, physiologic-, or pharmaceutically-acceptable diluent or carrier (see below).

Pharmaceutical Compositions and Methods of Treatment

A compound that is found to prevent or suppress amyloid beta-induced toxicity or the formation of amyloid beta aggregates in a cell can be formulated as a pharmaceutical composition, e.g., for administration to a subject to treat a neurodegenerative disease such as Alzheimer's disease.

A pharmaceutical composition typically includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge et al., J. Pharm. Sci. 66:1-19, 1977).

The compound can be formulated according to standard methods. Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X).

In one embodiment, a compound that prevents or suppresses amyloid beta-induced toxicity and/or amyloid beta aggregate formation in a cell can be formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

The pharmaceutical compositions may be in a variety of forms. These include, for example, liquid, semi-solid and solid dosage forms, such as liquid solutions (e.g., injectable and infusible solutions), dispersions or suspensions, tablets, capsules, pills, powders, liposomes and suppositories. The preferred form can depend on the intended mode of administration and therapeutic application. In some embodiments, compositions for the agents described herein are in the form of injectable or infusible solutions.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating a compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of a compound plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the compound can be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York, 1978.

A compound identified as one that prevents or suppresses amyloid beta-induced toxicity and/or amyloid beta aggregate formation in a cell can be modified, e.g., with a moiety that improves its stabilization and/or retention in circulation, e.g., in blood, serum, or other tissues, e.g., by at least 1.5, 2, 5, 10, or 50 fold. The modified compound can be evaluated to assess whether it can reach treatment sites of interest (e.g., locations of aggregate amyloid beta) such as can occur in a cell in a subject with a neurodegenerative disease such as Alzheimer's disease (e.g., by using a labeled form of the compound).

For example, the compound can be associated with a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used. For example, a compound can be conjugated to a water soluble polymer, e.g., a hydrophilic polyvinyl polymer, e.g., polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; and branched or unbranched polysaccharides.

When the compound is used in combination with a second agent (e.g., any additional therapies for Alzheimer's disease), the two agents can be formulated separately or together. For example, the respective pharmaceutical compositions can be mixed, e.g., just prior to administration, and administered together or can be administered separately, e.g., at the same or different times.

Compounds identified as described herein can be used to treat a subject (e.g., a human subject) that is at risk for or has a disorder associated with amyloid beta mediated toxicity and/or the formation, deposition, accumulation, or persistence of amyloid beta aggregates, e.g., amyloid beta oligomers and/or dimers. In certain embodiments, the disorder is Alzheimer's disease, Down's Syndrome, Fragile X syndrome, or systemic amyloidosis. Methods of identifying an individual at risk for or having such disorders are known in the art. For example, AD can be diagnosed based on, e.g., patient history (e.g., memory loss) clinical observations, the presence of characteristic neurological and neuropsychological features, and the absence of other conditions that might be responsible for the foregoing. Imaging techniques such as computed tomography (CT), magnetic resonance imaging (MRI), single photon emission computed tomography (SPECT), or positron emission tomography (PET) can be of use. Diagnosis can be confirmed by post-mortem examination of brain material. Exemplary criteria for diagnosis of AD are found in the Diagnostic and Statistical Manual of Mental Disorders (DSM)-IV (text revision, 2000) or DSM-V and the National Institute of Neurological and Communicative Disorders and Stroke (NINCDS)-Alzheimer's Disease and Related Disorders Association (ADRDA) criteria (McKhann G, et al. (1984) Neurology 34 (7): 939-44), e.g., as updated (Dubois B, et al. (2007) Lancet Neurol 6 (8): 734-46). Analysis of cerebrospinal fluid (CSF) for various biomarkers, e.g., amyloid beta or tau proteins (e.g., total tau protein and phosphorylated tau) and/or imaging (e.g., PET imaging) with labeled compounds that bind to amyloid beta deposits (e.g, 11C-labeled Pittsburgh Compound-B (11C-PIB) or 18F-AV-45 (flobetapir F18)) can be used to predict the onset of AD, e.g., to identify individuals who have a significant likelihood of progressing to AD in the future (e.g., within the next two years). Such imaging methods may also be of use in the instant invention to assess the in vivo effect of compounds identified herein. In some embodiments, a subject has a mutation in a gene encoding amyloid precursor protein (APP), presenilin 1, or presenelin 2. In some embodiments, the mutation increases the production of A$\beta$42 or alters the ratio of A$\beta$42 to A$\beta$40. In some embodiments the subject has at least one copy of the $\epsilon$4 allele of the apolipoprotein E (APOE) gene.

Downs' Syndrome can be diagnosed based on presence of trisomy 21.

Fragile X Syndrome is caused by expansion of a trinucleotide gene sequence (CGG) on the X chromosome that results in a failure to express the protein coded by the FMR1 gene, which encodes FMRP. It may be suspected based on the presence of characteristic signs and symptoms, with diagnostic confirmation from genetic testing.

Thus, methods and compositions for treating a subject at risk of (or susceptible to) an amyloid beta mediated disease are described herein. For example, an individual who is at risk of developing AD and/or has signs suggesting that he or she will develop AD can be treated with the compounds and methods described herein.

As used herein, the term "treatment" is defined as the application or administration of a therapeutic compound to a patient, or application or administration of a therapeutic compound to a subject (e.g., a human subject, who may be referred to as a "patient") who has a disease (or other medically recognized disorder or syndrome), a symptom of disease or a predisposition toward a disease (e.g., one or more risk factors associated with the disease), with the purpose to cure, heal, alleviate, relieve, alter, remedy, ameliorate, improve, or affect (in a manner beneficial to the subject) the disease, the symptoms of disease or the predisposition toward disease. In some embodiments, treatment is prophylactic, i.e., it is administered to a subject who has not developed the disease (and who may or may not have a predisposition to develop the disease) with an intent to delay, prevent, or reduce the likelihood that the subject will develop the disease or reduce the severity should the subject develop the disease. Compounds may also or alternately be administered to a subject for purposes of testing, research, or diagnosis and/or may be contacted with an isolated tissue, cells, or cell line from a patient, e.g., for purposes of testing, research, diagnosis, or with an intent to subsequently administer the isolated tissue, cells, or cell line to the subject for treatment.

The following are examples of the practice of the invention. They are not to be construed as limiting the scope of the invention in any way.

EXAMPLES

Example 1

Yeast Model of Amyloid Beta Toxicity

Several yeast strains were generated that enable inducible expression of the human amyloid beta 1-42 peptide. The expression construct used in these studies encodes a fusion polypeptide containing the yeast Kar2p signal sequence at the amino terminus and the human amyloid beta 1-42 peptide at the carboxy terminus. A signal sequence was included in the fusion polypeptide to cause the transport of the human amyloid beta 1-42 peptide to the endoplasmic reticulum within the cell. The polypeptide was expressed in yeast under the control of a galactose-inducible promoter.

The amino acid sequence of the fusion polypeptide encoded by the expression construct is: MFFNRLSAGKLL-VPLSVVLYALFVVILPLQNSFHSSNVLVRGDAEFRH DSGYEVHHQKLVFFAEDVGSNKGAIIGLMVGGVVIA (SEQ ID NO:1). The yeast Kar2p signal sequence corresponds to amino acids 1-42 of SEQ ID NO:1 and the human amyloid beta 1-42 peptide corresponds to amino acids 43-84 of SEQ ID NO:1.

The nucleotide sequence used in the expression construct is:

```
                                              (SEQ ID NO: 2)
ACAAGTTTGTACAAAAAAGCAGGCTTCACAAAATGTTTTTCAACAGACT

AAGCGCTGGCAAGCTGCTGGTACCACTCTCCGTGGTCCTGTACGCCCTT

TTCGTGGTAATATTACCTTTACAGAATTCTTTCCACTCCTCCAATGTTT

TAGTTAGAGGTGATGCTGAATTTAGACATGATTCTGGTTATGAAGTTCA

TCATCAAAAATTGGTTTTTTTTGCTGAAGATGTTGGTTCTAATAAAGGT

GCTATTATTGGTTTGATGGTTGGTGGTGTTGTCATTGCTTAAACCCAGC

TTTCTTGTACAAAGTGGT.
```

The region of SEQ ID NO:2 encoding the fusion polypeptide of SEQ ID NO:1 corresponds to nucleotides 33 to 284 of SEQ ID NO:1.

Western blot analysis demonstrated that the fusion polypeptide was processed when expressed in yeast cells to yield the human amyloid beta 1-42 peptide. The amount of the A amyloid beta 1-42 peptide detected within a cell correlated with the number of copies of the expression construct that were introduced into the cell.

The effect of expression of the fusion polypeptide on yeast cell viability was assessed. Yeast cells were transformed with either an empty vector or a galactose-inducible expression plasmid encoding the fusion polypeptide of SEQ ID NO:1. Serial dilutions of transformants were spotted on glucose or galactose and growth was assessed. Expression of amyloid beta 1-42 peptide (i.e., in transformants grown on galactose plates) was found to be highly toxic to yeast cells (FIG. 1; within each photograph, the empty vector is on the top and the experimental expression vector is on the bottom). The degree of toxicity increased with the number of copies of the expression construct that was introduced into a cell. The yeast cells depicted in the bottom two rows of FIG. 1 ("multiple copies") contain multiple integrated copies of the expression construct. Although the precise number of copies present in these cells is not known, the enhanced toxicity detected is presumed to be the result of a high copy number of the expression plasmid.

Figure 2:
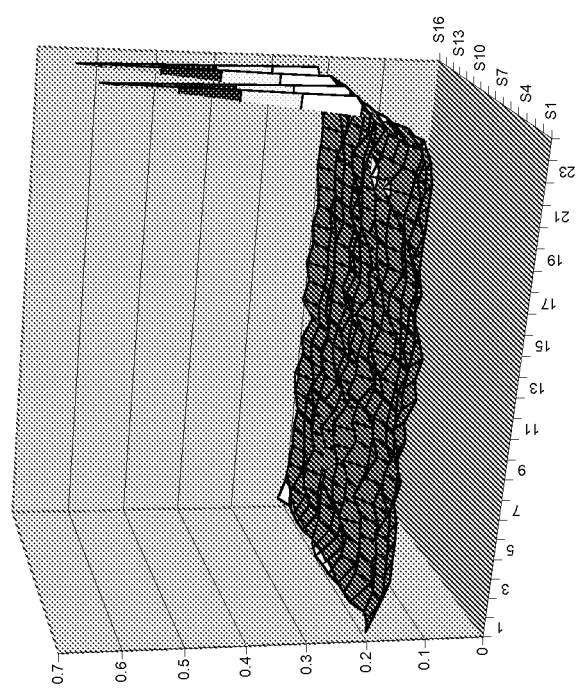
FIG. 2 is a three dimensional graph depicting the results of a screen to identify compounds that suppress toxicity induced by expression of a yeast Kar2p signal sequence/human amyloid beta 1-42 fusion polypeptide.

The amyloid beta-expressing yeast cells were used in a screening assay to assess the utility of the recombinant cells in screening for candidate therapeutic compounds. The screen included the following steps: cells were grown in raffinose; cells were diluted to 0.050 in galactose medium (to initiate expression of the expression construct); cells were distributed in a 384 well format; test compounds were added to the wells at a 10 uM final concentration; cell were grown for 48 hours; and the plates were read at A600. The screen identified two wells on the plate as exhibiting growth rescue in the presence of a test compound (FIG. 2). Each of these two wells contained the identical combination of clioquinol and iron (at concentrations of 5 uM each). Clioquinol is a known candidate compound for the treatment of Alzheimer's disease. The results of this screening assay demonstrate that yeast can be used as a model system for amyloid beta-induced cellular toxicity and that candidate therapeutic compounds can be identified that alleviate this toxicity.

Example 2

Detection of Aβ 1-42 in the Yeast Secretory System

Figure 3:
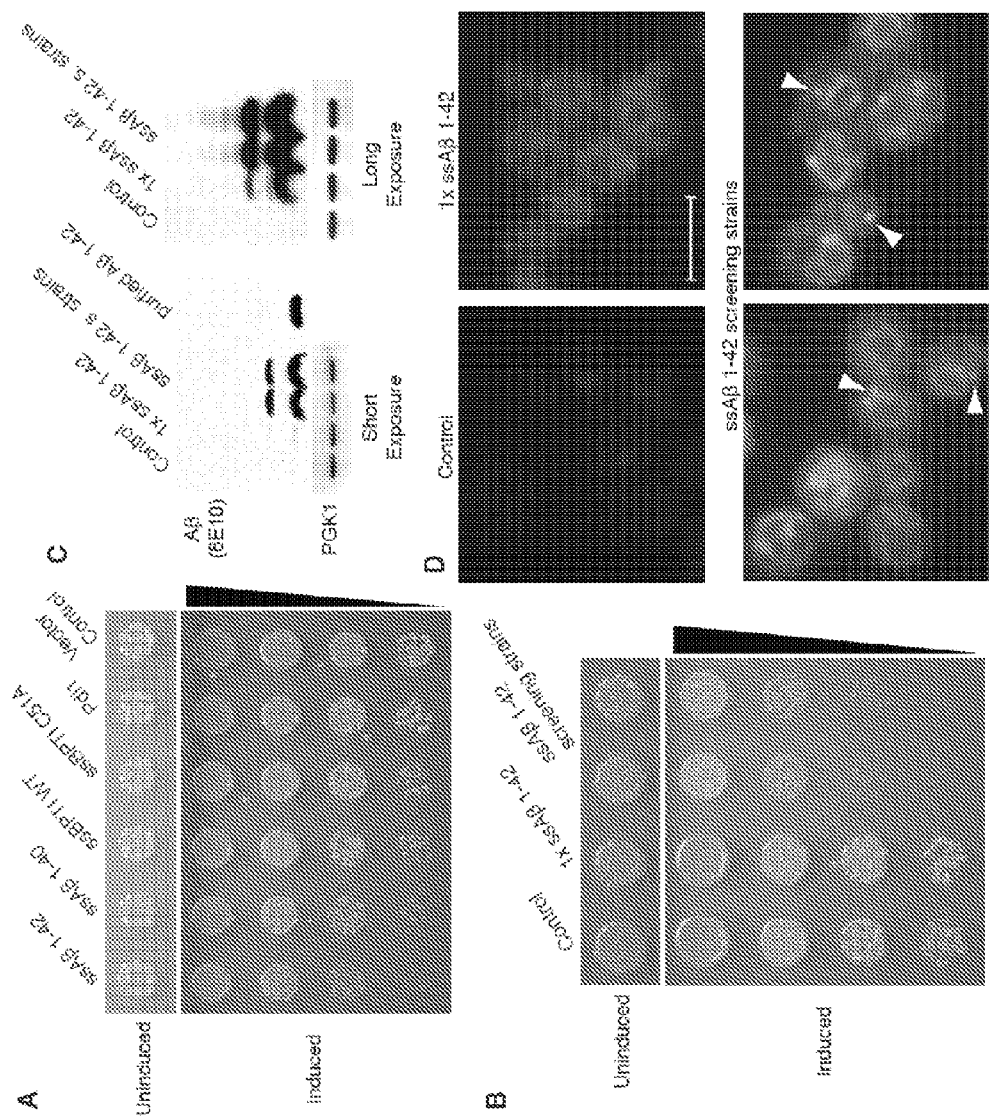
FIG. 3 is a series of photographs depicting an analysis of expression of yeast Kar2p signal sequence/human amyloid beta 1-42 fusion polypeptide (also referred to herein as "ssAβ 1-42") in yeast. (A) Comparison of yeast Kar2p signal sequence/human amyloid beta 1-42 fusion polypeptide (also referred to herein as "ssAβ 1-42") to yeast Kar2p signal sequence/human amyloid beta 1-40 fusion polypeptide (also referred to herein as "ssAβ 1-40"), ssBPTI (WT and C51A) and Pdi1. ssAβ 1-42 was more toxic than ssAβ 1-40 and other proteins targeted to the secretory pathway in the same manner as ssAβ. Proteins were expressed using the inducible GAL promoter and a high copy number plasmid. Strains carrying the plasmids were serially diluted and spotted on inducing (Galactose) and non-inducing (Glucose) media. (B) Construction of ssAβ 1-42 strains used in genetic screen. Expression of ssAβ 1-42 from a single integrated genomic copy was not toxic, but integration of several copies of the construct resulted in robust toxicity. (C) Aβ 1-42 expression in these strains was detected by immunoblot analysis using the 6E10 Aβ antibody. Longer exposure revealed the formation of higher molecular weight species consistent with the formation of Aβ oligomers and dimers. (D) Immunostaining for ssAβ 1-42 reveals localization to the endoplasmic reticulum (ER). Aβ was detected in the ER (ring surrounding the nucleus stained blue using DAPI) and in small foci throughout the cell (arrowheads). These foci may represent Aβ aggregates or accumulation in vesicles.
Figure 5:
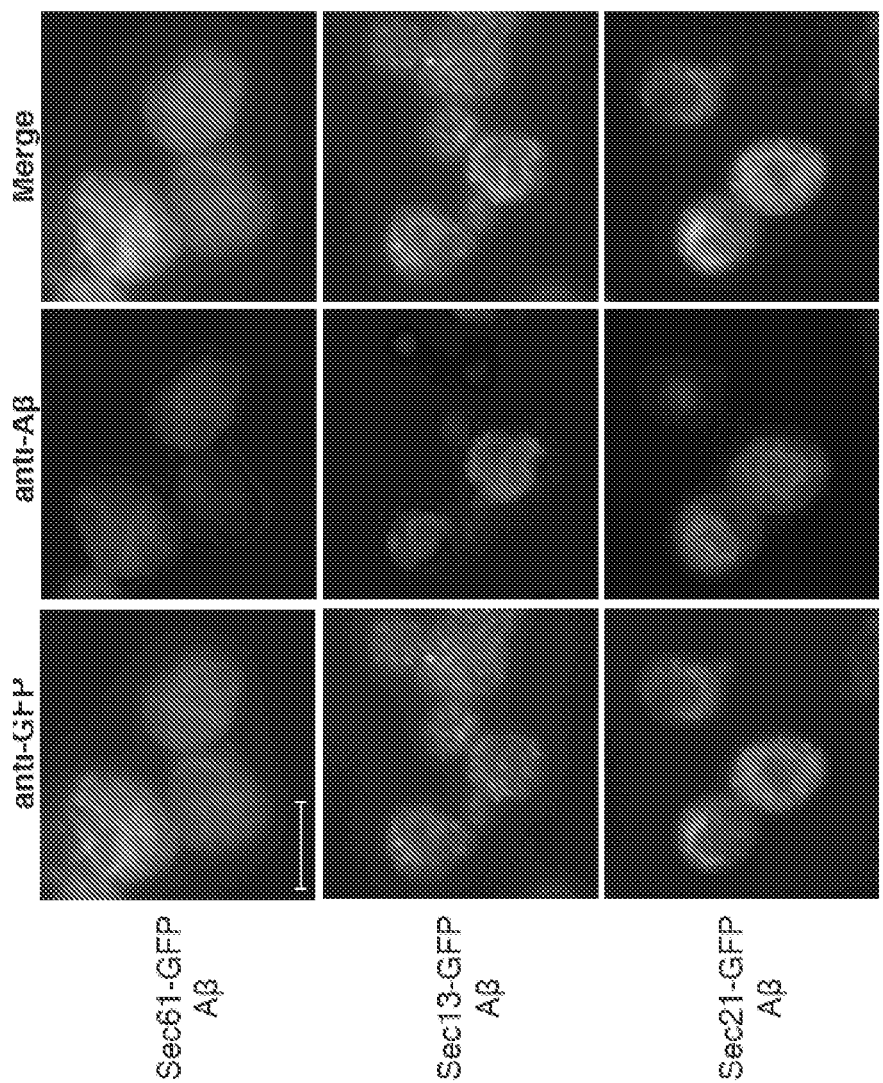
FIG. 5 is a series of photographs depicting localization of Abeta to the ER. ssAbeta was expressed using GAL inducible high copy number plasmid in the indicated GFP-tagged strains. Co-immunostaining for Sec61-GFP and Abeta shows co-localization of Abeta with an ER marker. Sec13 and Sec21 are markers for ER-Golgi vesicles. Abeta shows weak co-localization with Sec21, but no co-localization with Sec13.

As mentioned above, the integrated constructs resulted in generation of the correct peptide and the formation of higher molecular weight species likely representing Aβ oligomers and dimers. Immunostaining confirmed the localization of Aβ in the secretory system (FIG. 3 and FIG. 5).

Example 3

Further Analysis of Clioquinol Rescue

Figure 4:
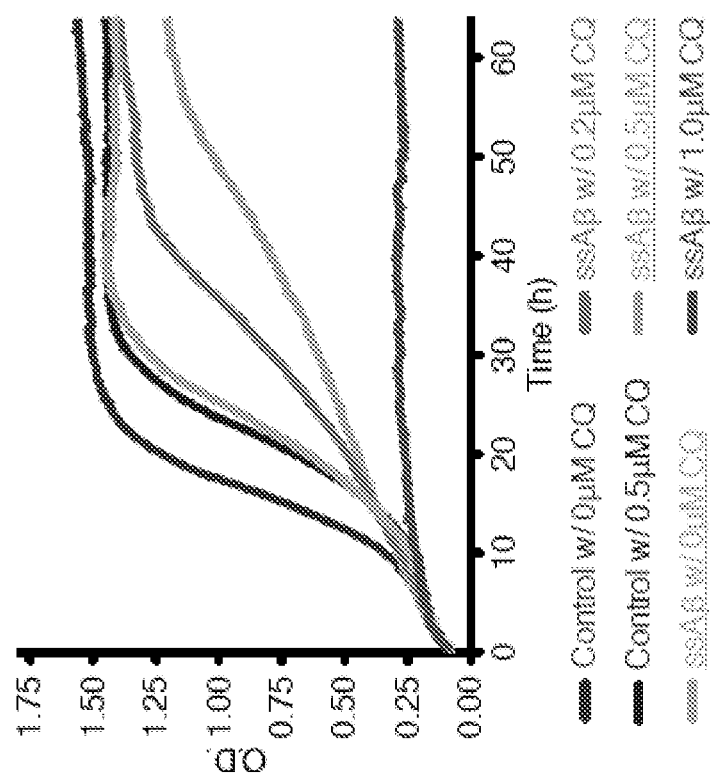
FIG. 4 is a graph depicting suppression of Aβ toxicity by clioquinol. Addition of clioquinol to a ssAβ 1-42 strain grown in inducing media rescued growth levels in a dose dependent manner. At the optimal concentration clioquinol restored growth levels to those of a control strain expressing YFP. At higher concentrations clioquinol became toxic to both strains.

To further test the effect of clioquinol, a control strain and a strain expressing toxic levels of Aβ were grown in liquid culture with various concentrations of the compound. Clioquinol improved the growth of the Aβ expressing strain in a dose dependent manner (FIG. 4). At the optimal concentration growth was nearly as robust as that of the control strain (FIG. 4). Importantly, clioquinol did not diminish GAL1-induced expression, as measured by flow cytometry of GAL controlled YFP (data not shown). The most effective concentration of clioquinol varied from 0.5 to 0.8 uM.

Example 4

Materials and Methods

Further Details Regarding Constructs, Strains and Growth Conditions

The ssAβ1-42 construct consists of attB sites for Gateway cloning the Kar2 signal sequence and the Aβ1-42 sequence. The Aβ sequence was codon optimized for expression in yeast. The entire construct was synthesized and cloned into the Gateway entry vector pDONR221.

The sequence of the ssAβ construct (SEQ ID NO: 2) is shown above. It will be appreciated that the sequence contains Gateway flanking regions at the 5' and 3' ends (nucleotides 1-32 and 288-312, respectively).

The same approach was used to generate the ssAβ1-40 construct. The BPTI WT and C51A constructs were the kind gift of Dane Wittrup (J. M. Kowalski, R. N. Parekh, K. D. Wittrup, Secretion efficiency in *Saccharomyces cerevisiae* of bovine pancreatic trypsin inhibitor mutants lacking disulfide bonds is correlated with thermodynamic stability. *Biochemistry* 37, 1264 (1998)). The original BPTI construct contains a signal sequence, but we replaced it with the Kar2 signal sequence in order to target them in the same manner as Aβ. The Kar2ss sequence and Gateway flanking regions were added to the BPTI ORFs using overlap extension PCR. The Pdi1 gene is part of the overexpression library used in the screen. The Pdi1 gene was gateway cloned into the pDONR221 entry vector. The Aβ and BPTI constructs as well as Pdi1 were cloned into the pAG Gal p426 vector (S. Alberti, A. D. Gitler, S. Lindquist, A suite of Gateway cloning vectors for highthroughput genetic analysis in *Saccharomyces cerevisiae*. *Yeast* 24, 913 (2007)). Constructs were transformed into W303 Mat α, can1-100, his3-11,15, leu2-3,112, trp1-1, ura3-1, ade2-1 using a standard lithium acetate transformation protocol.

To generate ssAβ1-42 screening strains the ssAβ1-42 construct was moved to a pAG Gal p305 expression vector (S. Alberti, A. D. Gitler, S. Lindquist, A suite of Gateway cloning vectors for highthroughput genetic analysis in *Saccharomyces cerevisiae*. *Yeast* 24, 913 (2007)). The plasmid was digested using BstX1, gel purified and transformed into W303. The transformation was carried out in duplicate and the level of growth of 16 transformants each was tested on synthetic deficient media lacking leucine with galactose. Two strains from the independent transformations where chosen as screening strains based on their robust yet intermediate toxicity that would allow for the identification of both suppressors and enhancers. Several transformants that showed no toxicity were chosen as 1xssAβ controls. The control strain for wild type yeast growth is carrying a Gal inducible YFP integrated in the same fashion as the ssAβ1-42 constructs. For spotting assays strains were grown over night at 30° C. in 3 ml SD media lacking the relevant amino acids and containing glucose. Cell concentrations (OD600) were adjusted in a 96-well plate to that of the strain with the lowest concentration. Cells were then 5 fold serially diluted and spotted on SD media containing glucose (Uninduced) and galactose (Induced). Plates were incubated at 30° C. for 2 (glucose) or 3 days (galactose).

Cell Lysis and Western Analysis

Strains were grown in synthetic deficient media lacking leucine and uracil (SD-Leu-Ura) with raffinose overnight at 30° C. Cultures were the diluted into inducing media containing galactose (OD600 0.2) and grown for 8 h. Cells were spun down for 5 min at 3,000 rpm. The supernatant was removed and the cells were resuspended in 200 ul lysis buffer (50 mM Hepes pH7.5, 150 mM NaCl, 2.5 mM EDTA, 1% Triton X-100, 50 mM NEM, 1 mM PMSF, 1 tablet Roche Complete Mini EDTA-free protease inhibitor cocktail/5 ml). Cells were kept on ice from this point on. Cells were transferred to an eppendorf tube containing ~200 ul glass beads and lysed by shaking for 3 min on a bead beater. Cell lysates were collected by puncturing the bottom of the eppendorf tube with a 20 gauge needle, sticking the punctured tube into a fresh tube and spinning them in a benchtop centrifuge at 6000 rpm for 15 seconds. 150 ul of cell lysate were collected and transferred to a new tube. Protein concentrations were measured using a BCA Bradford assay and equalized to the levels of the sample with the lowest concentration. 100 ul of the equalized lysates were then mixed with 2xSDS sample buffer (Laemmli buffer) and boiled for 5 min. Samples were run on Invitrogen NuPage Novex 4-12% Bis-Tris gels using MES SDS running buffer. Proteins were transferred to PVDF using a semi-dry transfer apparatus. For blots shown in FIG. 2, membranes were blocked with 5% milk 1xPBS, and subsequently probed with the mouse monoclonal anti-Aβ antibody 6E10 (Signet laboratories) at a dilution of 1:1,000. Blots were subsequently reacted with the antimouse IgG peroxidase conjugate (Sigma) at a dilution of 1:1,000. Blots were developed with either Super Signal West Pico Chemiluminescent Substrate (Thermo Scientific) or with Immobilon Western Chemiluminescent HRP Substrate (Millipore). For the loading control, blots were probed with a mouse monoclonal anti-PGK1 antibody at a dilution of 1:2,000 (Molecular Probes). For the Western Blots showing the effect of the human homologs on Ab levels, membranes were blocked with 5% milk 1xPBS, probed with the mouse monoclonal anti-Aβ antibody 6E10 (Signet laboratories) at a dilution of 1:1,000. Blots were subsequently reacted with the antimouse secondary antibody DyLight 800 (Rockland Immunochemicals) at 1:10,000. For the loading control, blots were probed with a mouse monoclonal anti-PGK1 antibody at a dilution of 1:2,000 (Molecular Probes). Blots were scanned using an Odyssey scanner (LI-COR Biosciences).

Immunostaining

Strains were pregrown in raffinose media overnight and then induced in galactose media for 8 hours (5 ml OD600 0.2). Cells were spun down and resuspended in 1 ml 3.7% formaldehyde (37% formaldehyde in 0.1M KPi (potassium phosphate buffer) pH6.4) after removal of supernatant. Cells were fixed over night at 4° C. After the fixation cells were washed three time in 1 ml 0.1M KPi pH 6.4 and then resuspended in 1 ml 1.2M sorbitol-citrate buffer (1 L: 218.6 g sorbitol, 17.40 g anyhydrorus K2HPO4, 7 g citric acid; filter sterilize). Cells were spun down again and resuspended in 200 ul of digestion mix (200 ul 1.2M sorbitol-citrate, 20 ul glusolase and 2 ul 10 mg/ml zymolase). Cells were incubated in the digestion mix for 45 min at 30° C. During the incubation 5 ul 0.1% polylysine was added to each well of a 30 well slide (Thermo ER-212W). After 5 min of incubation the slides was washed with distilled water and allowed to air dry completely. Digested cells were spun down at 3,000 rpm for 3 min and gently resuspended in 1 ml sorbitol-citrate. Cells were spun down again and then resuspended in a volume of sorbitol citrate dependent on cell pellet size (15-50 ul). 5 ul of cells was added to each well and incubated for 10 min. Cells were removed from the side of the well using a vacuum tip. If the cell density was low, as revealed by light microscopy, more cells were added. The slides were then incubated in ice-cold methanol for 3 min, followed by 10 sec in ice-cold acetone. Acetone was shook off and slides air-dried. As the primary antibody 4 ul of 1:200 6E10 in PBS/BSA (1% BSA, 0.04M K2HPO4, 0.01M KH2PO4, 0.15M NaCl, 0.1% NaN3; for 100 ml: 1 g BSA, 4 ml 1M K2HPO4, 1 ml 1M KH2PO4, 15 ml 1M NaCl, 1 ml 10% NaN3, sterilized water to 100 ml) were added to each well. Slide was incubated over night at room temperature in a wet chamber. After the incubation the antibody was removed using a vacuum tip and each well was washed 3 times with PBS/BSA. Then 4 ul of the secondary antibody, 1:100 anti-mouse FITC, was added to each well and incubated for 2 hours. Subsequently, each well was washed 4 times with PBS/BSA. 1 ul of DAPIMOUNT was added to each well prior to adding the coverslip and sealing the slide with nail polish. For co-immunostaining cells were processed as described above but incubated with 1:200 6E10 and 1:100 rabbit anti-GFP in PBS/BSA and subsequently 1:100 antimouse Alexa Fluor 594 and 1:100 anti-rabbit Alexa Fluor 488 in PBS/BSA simultaneously. The GFP-tagged strains are part of the yeast GFP library (R. Howson et al., Construction, verification and experimental use of two epitope tagged collections of budding yeast strains. *Comp Funct Genomics* 6, 2 (2005)). Images were taken on a Zeiss Aviovert. Final images were assembled from the different channels (GFP, DAPI and dsRed) in Adobe Photoshop. Brightness and contrast were adjusted equally for all images.

Clioquinol Rescue

Yeast strains were grown overnight to saturation in synthetic medium with glucose as the carbon source after inoculation from a colony. These cultures were used to inoculate raffinose cultures. Raffinose cultures in log phase growth (OD600 0.7-0.9) were diluted to an OD600 of 0.03 in synthetic medium with galactose as the carbon source, and 300 ml of the cell suspension was distributed to each well of a Bioscreen plate. 3.03 ml of clioquinol (Sigma C8133, ~95%), dissolved in DMSO at 100 times the final intended concentration, was added to each well. A Labsystems Bioscreen C was used to maintain the plate at 30 degrees C. and make OD600 measurements on each well at 10-minute intervals over a period of approximately three days. Each condition was performed in duplicate. The most effective concentration of clioquinol is slightly variable. In our experiments the most effective concentration varied from 0.5 to 0.8 uM.

OTHER EMBODIMENTS

It is to be understood that, while the invention has been described in conjunction with the detailed description thereof, the foregoing description is intended to illustrate and not limit the scope of the invention. It is also to be understood that claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all embodiments in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise and such embodiments do not constitute added matter or extend beyond the content of the application as filed. Where elements are presented as lists, it is to be understood that each subgroup of the elements is also disclosed, and any one or more element(s) can be removed from the group, and such subgroup or resulting list is explicitly disclosed herein and does not constitute added matter or extend beyond the content of the application as filed. It should it be understood that, in general, where the invention, or aspects of the invention, is/are referred to as comprising particular elements, features, etc., certain embodiments of the invention or aspects of the invention consist, or consist essentially of, such elements, features, etc. It should also be understood that any embodiment of the invention, can be explicitly excluded from the claims without constituting added matter or extending beyond the content of the application as filed. Other aspects, advantages, and modifications of the invention are within the scope of the claims set forth below.

What is claimed is:

1. A yeast cell comprising at least three copies of an expression construct comprising a promoter operably linked to a nucleic acid encoding a polypeptide comprising a signal sequence and a human amyloid beta protein, wherein expression of the nucleic acid and production of the polypeptide in the cell results in a decrease in growth or viability of the cell.

2. The yeast cell of claim 1, wherein expression of the nucleic acid and production of the polypeptide renders the cell non-viable.

3. The yeast cell of claim 1, wherein the expression construct is integrated in the genome of the yeast cell.

4. The yeast cell of claim 1, wherein the expression construct is an integrative plasmid.

5. The yeast cell of claim 1, wherein the signal sequence is identical to the signal sequence of a naturally occurring yeast protein.

6. The yeast cell of claim 5, wherein the signal sequence is identical to the yeast Kar2p signal sequence.

7. The yeast cell of claim 1, wherein the signal sequence is identical to the signal sequence of a naturally occurring mammalian protein.

8. The yeast cell of claim 7, wherein the mammalian protein is a human protein.

9. The yeast cell of claim 1, wherein the human amyloid beta protein is selected from the group consisting of wild type amyloid beta 1-38, wild type amyloid beta 1-39, wild type amyloid beta 1-40, wild type amyloid beta 1-41, wild type amyloid beta 1-42, and wild type amyloid beta 1-43.

10. The yeast cell of claim 1, wherein the human amyloid beta protein is selected from the group consisting of amyloid beta 1-38, amyloid beta 1-39, amyloid beta 1-40, amyloid beta 1-41, amyloid beta 1-42, and amyloid beta 1-43 and comprises a mutation selected from the group consisting of A2T, H6R, D7N, A21G, E22G, E22Q, E22K, D23N, A42T, and A42V.

11. The yeast cell of claim 1, wherein the human amyloid beta protein is wild type amyloid beta 1-42.

12. The yeast cell of claim 1, wherein the signal sequence is identical to the signal sequence of a naturally occurring yeast protein and the human amyloid beta protein is wild type amyloid beta 1-42.

13. The yeast cell of claim 1, wherein the signal sequence is identical to the yeast Kar2p signal sequence and the human amyloid beta protein is wild type amyloid beta 1-42.

14. The yeast cell of claim 1, wherein the polypeptide comprises the amino acid sequence of SEQ ID NO:1.

15. The yeast cell of claim 1, wherein the polypeptide consists of the amino acid sequence of SEQ ID NO:1.

16. The yeast cell of claim 1, wherein the nucleic acid comprises nucleotides 33 to 284 of SEQ ID NO:2.

17. A method of inducing toxicity in a yeast cell, the method comprising: providing the cell of claim 1; and inducing a level of expression of the nucleic acid in the yeast cell that is toxic to the yeast cell.

18. A method of identifying a compound that prevents or suppresses amyloid beta-induced toxicity, the method comprising:
culturing the cell of claim 1 in the presence of a candidate agent and under conditions that allow for expression of the nucleic acid at a level that, in the absence of the candidate agent, is sufficient to induce toxicity in the cell;
measuring cell growth or viability in the presence of the candidate agent; and
comparing cell growth or viability measured in the presence of the candidate agent to cell growth or viability in the absence of the candidate agent,
wherein if cell growth or viability is increased in the presence of the candidate agent as compared to in the absence of the candidate agent, then the candidate agent is identified as a compound that prevents or suppresses amyloid beta-induced toxicity.

19. A method of identifying a genetic suppressor or enhancer of amyloid beta-induced toxicity, the method comprising:
providing the yeast cell of claim 1, wherein the yeast cell has been genetically modified to overexpress a gene;
culturing the yeast cell under conditions that allow for expression of the protein at a level that, in the absence of overexpression of the gene, is sufficient to induce toxicity in the yeast cell;
measuring cell growth or viability in the presence of overexpression of the gene; and
comparing cell growth or viability measured in the presence of overexpression of the gene to cell growth or viability in the absence of overexpression of the gene,
wherein (i) if cell growth or viability is increased in the presence of overexpression of the gene as compared to in the absence of overexpression of the gene, then the gene is identified as a genetic suppressor of amyloid beta-induced toxicity, and (ii) if cell growth or viability is decreased in the presence of overexpression of the gene as compared to in the absence of overexpression of the gene, then the gene is identified as a genetic enhancer of amyloid beta-induced toxicity.

20. A method of identifying a genetic suppressor or enhancer of amyloid beta-induced toxicity, the method comprising:
providing the yeast cell of claim 1, wherein an endogenous gene of the yeast cell has been disrupted;
culturing the yeast cell under conditions that allow for expression of the protein at a level that, in the absence of disruption of the endogenous gene, is sufficient to induce toxicity in the yeast cell;
measuring cell growth or viability in the presence of disruption of the endogenous gene; and
comparing cell growth or viability measured in the presence of disruption of the endogenous gene to cell growth or viability in the absence of disruption of the endogenous gene,
wherein (i) if cell growth or viability is increased in the presence of disruption of the endogenous gene as compared to in the absence disruption of the endogenous gene, then the gene is identified as a genetic enhancer of amyloid beta-induced toxicity, and (ii) if cell growth or viability is decreased in the presence of disruption of the endogenous gene as compared to in the absence disruption of the endogenous gene, then the gene is identified as a genetic suppressor of amyloid beta-induced toxicity.

21. A yeast cell comprising an expression construct comprising a promoter operably linked to a nucleic acid encoding a polypeptide comprising a signal sequence and a human amyloid beta protein, wherein expression of the nucleic acid and production of the polypeptide in the cell results in a decrease in growth or viability of the cell, wherein the yeast cell is selected from the group consisting of *Saccharomyces cerevisiae*, *Schizosaccharomyces pombe*, and a *Candida* spp.

* * * * *

UNITED STATES PATENT AND TRADEMARK OFFICE
CERTIFICATE OF CORRECTION

PATENT NO. : 9,677,079 B2  
APPLICATION NO. : 13/521966  
DATED : June 13, 2017  
INVENTOR(S) : Kent E. S. Matlack, Susan L. Lindquist and Sebastian Treusch Page 1 of 1

It is certified that error appears in the above-identified patent and that said Letters Patent is hereby corrected as shown below:

On the Title Page

<u>Column 1</u>
Item (73), Delete "Insititute" and insert -- Institute --.

Signed and Sealed this
Twenty-fifth Day of February, 2020

Andrei Iancu
*Director of the United States Patent and Trademark Office*